US011896796B2

(12) United States Patent
Vasko et al.

(10) Patent No.: US 11,896,796 B2
(45) Date of Patent: *Feb. 13, 2024

(54) DISPOSABLE INTRAVENOUS (IV) SET WITH FLOW CONTROL VALVE

(71) Applicant: CareFusion 303, Inc., San Diego, CA (US)

(72) Inventors: Robert Vasko, San Diego, CA (US); Stephen J. Bollish, San Diego, CA (US); Lawrence Farhat, Oceanside, CA (US); Daniel Abal, San Diego, CA (US); Robert Dwaine Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 667 days.

This patent is subject to a terminal disclaimer.

(21) Appl. No.: 16/858,348

(22) Filed: Apr. 24, 2020

(65) Prior Publication Data

US 2020/0254233 A1    Aug. 13, 2020

Related U.S. Application Data

(63) Continuation of application No. 15/394,725, filed on Dec. 29, 2016, now Pat. No. 10,632,299.

(Continued)

(51) Int. Cl.
*A61M 39/24* (2006.01)
*A61M 5/14* (2006.01)
(Continued)

(52) U.S. Cl.
CPC .............. *A61M 39/24* (2013.01); *A61M 5/14* (2013.01); *A61M 5/142* (2013.01);
(Continued)

(58) Field of Classification Search
CPC ...... A61M 39/24; A61M 5/14; A61M 5/1413; A61M 5/142; A61M 5/31; A61M 25/0606;
(Continued)

(56) References Cited

U.S. PATENT DOCUMENTS 3,385,301 A    5/1968    Harautuneian
4,306,705 A    12/1981    Svensson
(Continued)

FOREIGN PATENT DOCUMENTS

CN        1083400 A    3/1994
CN        1171746 A    1/1998
(Continued)

OTHER PUBLICATIONS

Extended European Search Report for Application No. 22150955.7, dated May 23, 2022, 7 pages.
(Continued)

*Primary Examiner* — Robert J Utama
*Assistant Examiner* — Hamza A Darb
(74) *Attorney, Agent, or Firm* — Morgan, Lewis & Bockius LLP

(57) ABSTRACT

A retrograde disposable intravenous (IV) set is disclosed. The IV set includes a diverter housing between upper and lower portions of a fluid line, the diverter housing including a lower end and an upper end extending away from the lower end and the fluid line to a syringe port located in the upper end, and a diverter member within the diverter housing and configured to move within the diverter housing from a first position, at which a first opening through the diverter member forms a first fluid pathway between the upper portion and the lower portion of the fluid line, to a second position, at which the first fluid pathway is blocked and a second fluid pathway is formed between the upper portion of (Continued)

the fluid line and a syringe port. Retrograde infusion may occur when the diverter member is in the second position.

20 Claims, 7 Drawing Sheets

Related U.S. Application Data

(60) Provisional application No. 62/273,962, filed on Dec. 31, 2015.

(51) Int. Cl.
*A61M 5/142* (2006.01)
*A61M 5/31* (2006.01)
*A61M 25/06* (2006.01)
*A61M 39/22* (2006.01)
*A61M 39/00* (2006.01)

(52) U.S. Cl.
CPC ............ *A61M 5/1413* (2013.01); *A61M 5/31* (2013.01); *A61M 25/0606* (2013.01); *A61M 39/22* (2013.01); *A61M 39/225* (2013.01); *A61M 2005/1403* (2013.01); *A61M 2005/1406* (2013.01); *A61M 2039/224* (2013.01); *A61M 2205/60* (2013.01); *A61M 2205/6018* (2013.01); *A61M 2205/6063* (2013.01)

(58) Field of Classification Search
CPC ................ A61M 39/22; A61M 39/225; A61M 2005/1403; A61M 2005/1406; A61M 2039/224; A61M 2205/60; A61M 2205/6018; A61M 2205/6063; A61M 39/223; A61M 2039/0018
See application file for complete search history.

(56) References Cited

U.S. PATENT DOCUMENTS

| 5,125,915 | A | | 6/1992 | Berry et al. |
| 5,195,986 | A | | 3/1993 | Kamen |
| 5,261,887 | A | | 11/1993 | Walker |
| 5,267,964 | A | * | 12/1993 | Karg ................... A61M 5/1424 604/141 |
| 5,935,105 | A | | 8/1999 | Manning et al. |
| 7,291,133 | B1 | | 11/2007 | Kindler et al. |
| 8,814,829 | B2 | | 8/2014 | Lal |
| 2003/0014035 | A1 | | 1/2003 | Trombley et al. |
| 2010/0292674 | A1 | | 11/2010 | Jepson et al. |
| 2012/0041416 | A1 | | 2/2012 | Lal |
| 2012/0185267 | A1 | | 7/2012 | Kamen et al. |
| 2013/0281966 | A1 | | 10/2013 | Susi |
| 2014/0124087 | A1 | * | 5/2014 | Anderson ............... A61M 5/19 141/2 |
| 2014/0303568 | A1 | | 10/2014 | Wiest et al. |
| 2015/0250947 | A1 | | 9/2015 | Davis |
| 2016/0243346 | A1 | * | 8/2016 | Vasko ................. A61M 5/1409 |

FOREIGN PATENT DOCUMENTS

| CN | 2535076 Y | 2/2003 |
| CN | 2624941 Y | 7/2004 |
| CN | 1561441 A | 1/2005 |
| CN | 1874808 A | 12/2006 |
| CN | 101356364 A | 1/2009 |
| CN | 202961319 U | 6/2013 |
| CN | 203816082 U | 9/2014 |
| GB | 1511842 A | 5/1978 |
| JP | H112265 A | 1/1999 |
| JP | 2008045669 A | 2/2008 |
| WO | WO-2005104687 A2 | 11/2005 |
| WO | WO-2010048644 A1 | 4/2010 |
| WO | WO-2012005134 A1 | 1/2012 |

OTHER PUBLICATIONS

Australian Office Action for Application No. 2016381963, dated Feb. 9, 2021, 4 pages.
European Office Action for Application No. 16826672.4, dated Feb. 24, 2021, 4 pages.
Chinese Office Action for Application No. 201680070277.9, dated Sep. 3, 2020, 21 pages.
International Search Report and Written Opinion for Application No. PCT/US2016/069335, dated Jun. 16, 2017, 23 pages.
Invitation to Pay Additional Fees and Partial Search Report for Application No. PCT/US2016/069335, dated Apr. 19, 2017, 6 pages.
Chinese Office Action for Application No. 201680070277.9, dated Apr. 27, 2021, 9 pages including translation.
Canadian Office Action for Application No. 3004489, dated Feb. 17, 2023, 5 pages.

* cited by examiner

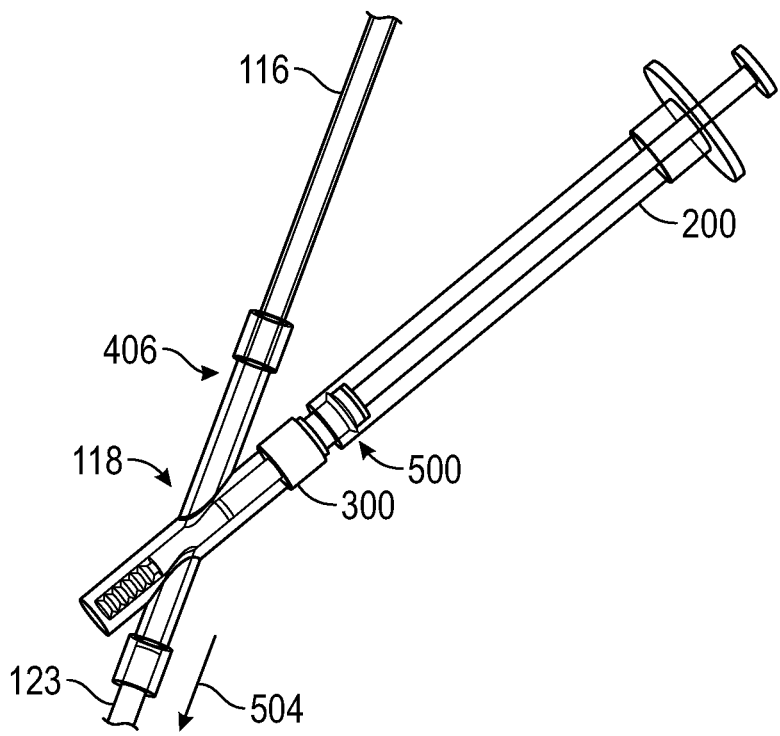
FIG. 5
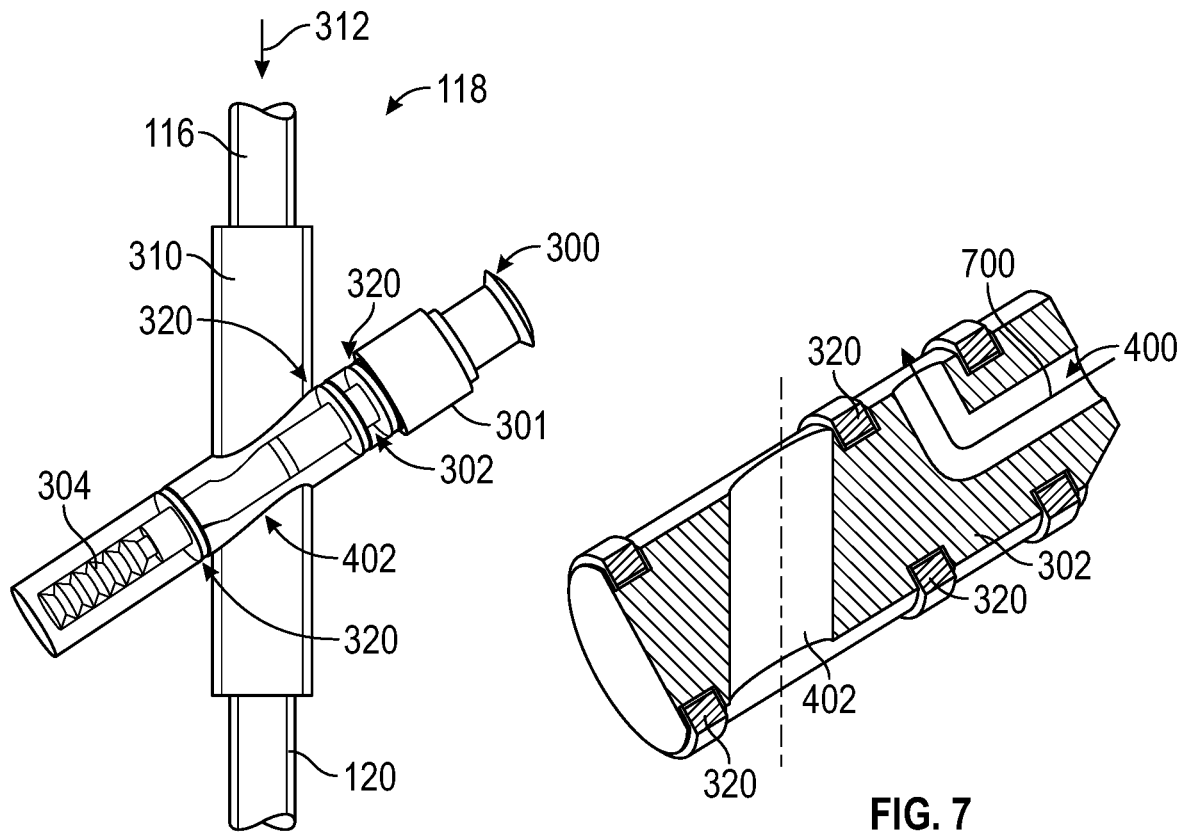
FIG. 6
FIG. 7

DISPOSABLE INTRAVENOUS (IV) SET WITH FLOW CONTROL VALVE

CROSS REFERENCE TO RELATED APPLICATIONS

This application is a continuation application of U.S. application Ser. No. 15/394,725, entitled "SYSTEMS AND METHODS FOR INTERMITTENT INFUSION," filed on Dec. 29, 2016, now U.S. Pat. No. 10,632,299, which is a non-provisional of U.S. Application No. 62/273,962, entitled "SYSTEMS AND METHODS FOR INTERMITTENT INFUSION," filed on Dec. 31, 2015, the entirety of each of which is incorporated herein by reference.

TECHNICAL FIELD

The present disclosure generally relates to the administration of medical fluid by infusion and, in particular, relates to systems and methods for providing and pumping medical fluid.

BACKGROUND

Infusion pumps have become commonplace within the healthcare industry as devices for precisely administering intravenous (IV) fluids. Use of a pump in place of an elevated fluid container with a simple roller clamp to control the flow of the IV fluid allows more accurate and consistent control of the rate of delivery of the fluid to the patient.

The assembly of tubing, valves, fittings, and catheters that connect the fluid container to the patient may be referred to as an "IV set." IV sets are typically disposable to reduce the risk of infection and contamination. In conventional infusion pump/IV set systems, a drug for delivery to the patient is typically provided at or above the pump. In these conventional systems, a fluid such as saline that fills the tubing between the pump and the patient is thus provided to the patient before any of the drug reaches the patent, which can cause an undesirable delay before the drug reaches the patient.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 5 illustrates a side view of a flow control valve and a syringe for attachment thereto according to certain aspects of the present disclosure.

FIG. 6 illustrates another side view of a flow control valve according to certain aspects of the present disclosure.

FIG. 7 illustrates a cross-sectional side view of a valve member of the flow control valve of FIG. 6 according to certain aspects of the present disclosure.

DETAILED DESCRIPTION

Figure 1:
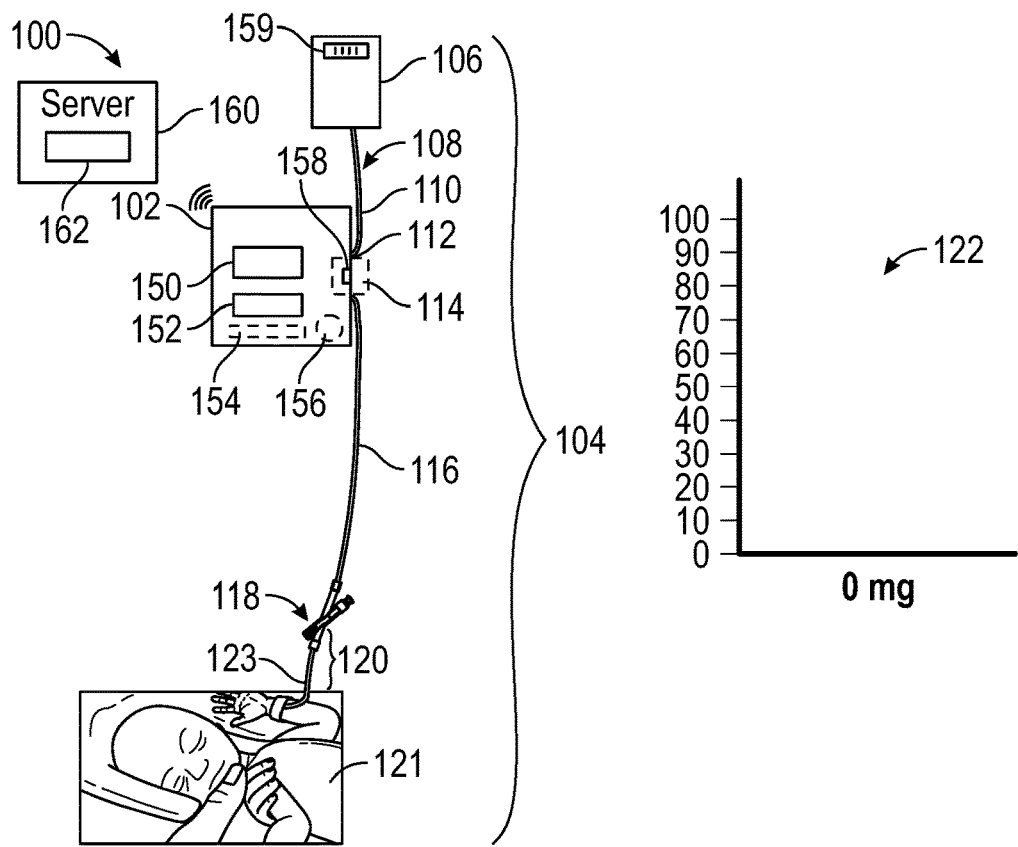
FIG. 1 is a diagram illustrating a system for administering medical fluid to a patient using an IV pump and an IV set having a flow control valve and a flush container according to certain aspects of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Delivery of very small volume intermittent IV medications (e.g., 0.2-2 mL volume deliveries) can be a difficult and time consuming task for clinicians caring for very small patients. According to some embodiments, small volume intermittent IV infusions are administered as a two-step process using a syringe pump. Two typical scenarios (a) and (b) for a two-step process follow:

In process (a), syringe administration set has been pre-primed with a flush fluid (typically normal saline) solution and the following operations 1a-8a may be performed:

1a.) a clinician disconnects current syringe, then attaches a syringe containing a small volume intermittent IV drug. The dose volume may be 0.8 mL and the priming volume of syringe set may be 0.5 mL. 2a.) The clinician programs a dose and a dose volume of 0.8 mL to be administered over 30 minutes. 3a.) Infusion is started and the dose volume of 0.8 mL is administered over the programmed 30 minutes (e.g., at a rate of 1.6 mL/h). After 30 minutes in this scenario, the patient has received 0.5 mL of saline that was in the line at the start of the infusion and an additional 0.3 mL of drug solution. The line still contains 0.5 mL of drug solution. 4a.) The clinician detaches the drug syringe and attaches a flush syringe containing normal saline. 5a.) The clinician programs a flush solution volume of 0.7 mL to be delivered at the same rate as the previous drug solution (e.g., at a rate of 1.6 mL/h). The clinician may also program an additional 0.2 mL of flush solution to completely flush the drug from the extension sets connected below the syringe set. The duration of the infusion in this scenario is approximately 26.5 minutes. 6a.) The infusion pump signals the completion of the infusion 7a.) The clinician returns to the bedside to reprogram a subsequent drug infusion, or to turn the pump off, or program a very low rate to keep the line open until the next infusion. 8a.) In this scenario, the entire dose of 0.8 mL has been delivered over approximately 56.5 minutes, not counting the delay for clinician having to return to the bedside. The patient has also received 0.7 mL of normal saline flush solution.

In process (b), a syringe administration set is primed with a drug solution and the following operations 1b-9b may be performed:

1b.) A clinician attaches a new unprimed administration set and primes the line with the drug solution. The dose volume may be 0.8 mL and a priming volume of syringe set may be 0.5 mL. At the completion of the priming process, there is 0.3 mL of drug left in the medication syringe and 0.5 mL of drug in the tubing set. 2b.) The clinician loads the syringe into the pump and attaches the end of the set to the patient extension set. The extension set may also contain 0.2 mL of normal saline. 3b.) The clinician programs a dose and a dose volume of, for example, 0.3 mL to be administered over 30 minutes. 4b.) The infusion is started by the pump and a dose volume of 0.3 mL is administered over the programmed 30 minutes (e.g., at a rate of 0.6 mL/h). In this scenario, the patient has received 0.1 mL of drug after the 0.2 mL of saline in the extension set has been cleared. The line and extension set still contains 0.7 mL of drug solution. 5b.) The clinician detaches the drug syringe and attaches a flush syringe containing normal saline. 6b.) The clinician programs a flush solution volume of 0.5 mL to be delivered at the same rate as the previous drug solution (e.g., at a rate of 0.6 mL/h). The clinician may program an additional 0.2 mL of flush solution to completely flush the drug from the extension sets connected below the syringe set. In this scenario, the duration of the infusion is 70 minutes. 7b.) The infusion pump signals the completion of the infusion. 8b.) The clinician returns to the bedside to reprogram a subsequent drug infusion, or to turn the pump off, or program a very low rate to keep the line open until the next infusion. 9b.) The entire dose of 0.8 mL has been delivered over 100 minutes, not counting the delay for clinician having to return to the bedside. The tubing and extension set now contain 0.7 mL of normal saline flush solution.

However, each of the above processes (a) and (b) utilize multiple breaks in the system to accommodate drug and flush solution attachment and each takes twice as long to deliver the drug compared to an exemplary desired delivery time of 30 minutes.

Moreover, in process (a) the patient received an extra 0.7 mL of normal saline in order to completely deliver the medication. In process (b), at the completion, the IV line is loaded with an extra 0.7 mL of normal saline. At the time of the next dose, the clinician can either replace the tubing with a new unprimed tubing, or revert to process (a). Using a new tubing is an added cost and an additional break in the system.

Moreover, in both process (a) and (b), a time consuming two phase delivery approach is performed with multiple trips back to the bedside for initial setup and then flush setup. This two phase setup makes for difficult application of Dose Error Reduction System (DERS) limits and difficult documentation either manual, or automated in the Medication Administration Record (MAR). Confusion can also result at the bedside since only the medication syringe is labeled with the drug name and other important information about the dose. The flush syringe typically does not contain labeling about the dose, so it may not be apparent to the clinician or another clinician what dose, or how much of the dose has been completed.

In various scenarios, patients may require multiple doses of multiple medications each day. Complete and on time delivery of the dose with minimal priming and flush solution is desired in order to assure good therapeutic outcome while minimizing the fluid intake for medication delivery so that sufficient fluid intake for other therapies and nutrition can be accomplished. Stated another way, each mL of drug and normal saline flush means the typically fluid-restricted Natal Intensive Care Unit (NICU) patient receives one less mL of life sustaining IV nutritional and other supporting therapies.

In a population of small patients (e.g., infants), it can also be difficult to obtain and maintain venous access, so it helpful to be able to efficiently and completely deliver intermittent medications in the shortest time that is safe, so that the limited IV access can be used for other interventions.

Efficient and effective use of Dose Error Reduction Software (DERS) may also be important in this patient population in order to assure correct dose and dose delivery times. Proper labeling at the bedside and documentation of administration into the Medication Administration Record (MAR) is also required. This patient population is also prone to hospital acquired infections associated with IV therapy. It is therefore desirable to minimize, or eliminate breaks (e.g., connect/disconnect cycles) in the IV system whenever possible.

According to various embodiments, systems and methods are disclosed for retrograde infusion of a volume smaller than the distal priming volume of a retrograde infusion set. The retrograde infusion systems and methods disclosed hereinafter may provide various benefits, in comparison with prior art infusion systems and with processes (a) and (b) above. For example, the systems and methods disclosed hereinafter may provide small volume and/or intermittent infusion in which only one break in the system is performed to deliver all phases of the infusion. The systems and methods disclosed hereinafter may also provide small volume and/or intermittent infusion in which the system (e.g., the infusion pump) prevents administration of a dose volume that is greater than the system is designed to support. The systems and methods disclosed hereinafter may also provide small volume and/or intermittent infusion in which one infusion setup is used for all phases of the delivery process (pre-prime, dose delivery and flush). The systems and methods disclosed hereinafter may also provide small volume and/or intermittent infusion in which no return trips to the bedside by the clinician are needed to program a flush. The systems and methods disclosed hereinafter may also provide small volume and/or intermittent infusion in complete delivery of the drug in the prescribed dose volume is provided without the need for additional normal saline flush solution delivered to the patient. The systems and methods disclosed hereinafter may also provide small volume and/or intermittent infusion in which a dose is delivered over the desired duration. The systems and methods disclosed hereinafter may also provide small volume and/or intermittent infusion in which a drug is delivered with full DERS protection for total the dose and total duration of infusion. The systems and methods disclosed hereinafter may also provide small volume and/or intermittent infusion in which all phases of the delivery process are displayed on the pump, thus helping to reduce or eliminate mix-ups or errors. The systems and methods disclosed hereinafter may also provide small volume and/or intermittent infusion in which the entire dose delivery process is seamlessly documented in the MAR.

According to various embodiments, microinfusions (e.g., the delivery of very small volumes (e.g., infusions of less than 5 mL) of fluid/medication to typically very small patients; also applies to very low rate (e.g., less than 2 mL/h rate infusions) may be provided using the systems and methods described herein.

FIG. 1 illustrates a system 100 for microinfusion of a medical fluid such as a drug, medication, or other medical fluid, to a patient 121. As shown in FIG. 1, system 100 may include an infusion pump 102 and an IV set 104 such as a retrograde infusion set. IV set 104 may include a flush solution container 106, a pump interface portion 112, a flow control valve 118, a set identifier 159 (e.g., a barcode or RFID tag), and a patient interface portion 120. Tubing such as flexible, elastomeric tubing 108 may extend from flush container 106 to flow control valve 118 via pump 102. The tubing 108 may include a first tubing portion 110 that extends from flush container 106 to pump interface portion 112 and a second tubing portion 116 that extends from pump interface portion 112 to flow control valve 118.

Pump interface portion 112 may be implemented as a portion of a continuous tubing segment that runs continuously from flush container 106 to flow control valve 118 in which tube interface portion 112 is merely a portion of the continuous tubing that is captured and manipulated by pump 102 in operation. In this implementation, pump 102 may include components configured to capture the tubing and selectively compress portions of the captured tubing (e.g., using peristaltic or other suitable pumping mechanisms) to move the fluid through the tubing. However, this is merely illustrative.

In another implementation, pump interface portion may include a pump cassette 114 coupled between tubing segments 110 and 116 and configured to be received in a cassette recess in pump 102. In this implementation, pump cassette 114 may include various valves, pistons, flow control pathways, and/or other components that can be manipulated by corresponding pump and/or valve actuators of pump 102 to pump fluid through IV set 104 in a forward direction (e.g., toward the patient 121) and/or a reverse direction (e.g., away from the patient 121 toward flush container 106).

Patient interface portion 120 may include an extension set and a venous access device (e.g., an IV catheter). Patient interface portion 120 may include tubing 123 that extends from flow control valve 118 to the venous access device. Tubing 123 may have a length that is substantially less than the length of tubing segment 116 so that a medical fluid to be provided to the patient can be provided without providing the entire volume of fluid (e.g., saline) already in tubing segment 116 to the patient.

Pump 102 may include a display 150, input/output components 152 (e.g., a keyboard or keypad, a touchscreen, a code scanner, an RFID reader, and/or one or more dials, buttons, or switches), internal circuitry such as processing circuitry 154, memory 156, and components 158, which may include pumping components and/or one or more sensors such as a pressure sensor. Memory 156 may store instructions or code that, when executed by processing circuitry 154 operates pump components 158 (e.g., one or more motors, pistons, etc.) to pump fluid through IV set 104. Memory 156 may also store IV set information for one or more IV set types each in associated with a set identifier or Set ID. Processing circuitry 154 may include communications components for wired or wireless communication with a remote server such as server 160. Server 160 may include a database that stores, for example, IV set information for one or more IV set types each in associated with a set identifier or Set ID.

Flow control valve 118 may include a first fluid pathway extending from tubing segment 116 to tubing 123. In the configuration shown in FIG. 1, flow control valve 118 allows fluid to flow through this first fluid pathway such that IV set 104 can be primed and loaded and a desired infusion can be programmed into pump 102.

Flow control valve 118 may also include an additional input port (e.g., a Luer port) configured for coupling to a syringe from which a desired medical fluid for microinfusion to the patient is received. Flow control valve 118 may be configured to prevent flow along the first fluid pathway when the syringe is coupled to the input port of the flow control valve and enable flow along a second fluid pathway from the attached syringe into tubing segment 116. Pump 102 may be configured to detect pressure generated by an injection from the syringe and begin pumping in a reverse direction (e.g., retrograde pumping) to help move fluid within tubing segment 110 into flush container 106 and move fluid from tubing segment 116 into tubing segment 110 to accommodate the injected medical fluid.

According to various embodiments, a retrograde infusion set 104 may be provided for microinfusion delivery of intermittent medications that may include a low prime volume upstream segment for connection to the syringe, or IV container, a cassette or other pump interfacing portion or device, and a very low priming volume microbore patient extension. The infusion set 104 may be provided with a set identifier (Set ID) 159 that identifies that individual set or the type of set. The volume contained between the cassette/interface and the lower flow control valve may be transmitted to the pump as part of the Set ID information or may be determined by the pump using the Set ID information (e.g., via lookup from an internal pump database or a remote database). In addition, a flow control valve 118 as described in further detail below is incorporated at the termination of the set. The pump 102 may be operated, at least in part, based on IV set information (e.g., a volume of a portion of the IV set below the pump) determined from the Set ID information. Examples of pump operations based on identified components of an infusion pump system can be found, for example, in U.S. Pat. Nos. 8,038,593 and 9,162,023 each of which is hereby incorporated by reference herein in its entirety.

According to some embodiments, an optional mechanical device or holder attached to the system may be provided that holds, for example, a 1-60 mL syringe in close proximity to a syringe set cassette. One holder would optionally be available for each infusion channel. These syringe holders may be provided to support a syringe connected to the upstream side (e.g., above the pump), the syringe acting as a substitute for an IV bag to provide flush and keep open IV solution.

Various aspects of a retrograde infusion of a volume smaller than the distal priming volume of a retrograde IV set are described hereinafter in accordance with various embodiments. In one example, a use case is described for exemplary steps involved in administering an intermittent medication via the system 100 in a retrograde fashion from a syringe that contains a volume that is smaller than the priming volume of the administration set below the pump chamber.

In this use case, a clinician determines that it is time to administer the prescribed dose of a drug such as Drug A to the patient based on a physician order and hospital protocol. The system 100 for this use case may include a clinical device 102 such as a two channel large volume pump (LVP) based infusion pump that has the capability to pull from bags, bottles and syringes. The system also incorporates a set ID system that allows the pump to determine whether a retrograde type of set has been installed and/or the retrograde volume (e.g., 2 mL in this exemplary use case) between the lower flow control valve 118 and the pump interface 112 or cassette 114. The pump incorporates processing circuitry 154 and pump components that provide for the ability of the pump to run forward and/or to run backward to allow retrograde flow into the retrograde set with a volume of fluid that is less than the distal priming volume of the retrograde set.

In this use case, the retrograde set 104 is a clinical device, designed for delivery of fluid from syringes in a retrograde fashion. The set is constructed of small bore tubing 116 below the cassette so as to minimize mixing of the drug and flush solutions at the interface of the two fluids.

In this use case, the medication syringe is a clinical device. The medication syringe is a disposable syringe that is filled (usually in a pharmacy) with the exact dose of medication to be delivered to the patient. The medication syringe is affixed with a label describing the syringe contents, concentration, expiration date, lot numbers, bar code, etc.

In this use case, the flow control valve 118 is a clinical device. The valve 118 is positioned at the patient side termination of the retrograde set 104. Valve 118 may be a needleless on/off valve that may include a shroud covering the injection port in one implementation. In this implementation, when the injection port is covered, the valve is in the open-to-patient position. In this implementation, when the injection port is exposed, it is automatically closed to the patient.

In this use case, preconditions for the retrograde infusion may include an order for a clinician to administer 100 mg of Drug A in a 0.4 mL volume over 30 minutes. In this use case, preconditions for the retrograde infusion may include system 100 being powered on and at the bedside and having an idle channel available for use. In this use case, preconditions for the retrograde infusion may include the system having a dataset and the correct care area for the patient has been selected (e.g., at pump 102). In this use case, preconditions for the retrograde infusion may include a configuration for the selected care area that has the following configuration parameters set for intermittent infusions: (a) a microinfusion prime feature is enabled in which a maximum microinfusion prime rate is configured to 20 mL/h, a default microinfusion prime rate is configured to 5 mL/h, a maximum microinfusion prime volume is configured to 1 mL, and a default microinfusion prime volume is configured to 0.2 mL; (b) a microinfusion post flush feature is enabled in which a default micro infusion post flush volume is 0.2 mL, (c) a library is setup for Drug A in the selected care area and has the following characteristics relevant to this use case: Drug A is setup as a microinfusion intermittent GR infusion in which In this use case, post-conditions for the retrograde infusion may include concentration is 250 mg/mL (e.g., a base concentration) and an initial duration for the 250 mg/mL concentration is 30 min. In this use case, preconditions for the retrograde infusion may include a primed (e.g., primed with normal saline) retrograde set such as set 104 loaded into channel A of the pump system and connected to the patient. In this use case, preconditions for the retrograde infusion may include a medication syringe containing 100 mg/0.4 mL of Drug A at the bedside and ready to be administered.

In this use case, post-conditions for the retrograde infusion may include Drug A (e.g., 100 mg/0.4 mL) having been completely delivered to the patient with no residual medication in the syringe set. For example, the dose has been delivered over 30 min with 2.4 minute pre-flush period. In this use case, post-conditions for the retrograde infusion may include the retrograde syringe set containing normal saline flush solution and being ready to be used to deliver subsequent intermittent infusion doses if supported by hospital protocol. Subsequent doses could be administered using all workflows described in this use case (e.g., syringe-above-cassette or retrograde). In this use case, post-conditions for the retrograde infusion may include system 100 having properly logged and reported the infusion events.

In this use case, the processes of the flow of operations may include a clinician selecting channel A of pump 102 (e.g., using input/output components 152) for programming. In this use case, the processes of the flow of operations may include a clinician programing channel A flush/keep open line. In this use case, the processes of the flow of operations may include a clinician selecting (e.g., using input/output components 152) a micro-infusion mode for pump 102. In this use case, the processes of the flow of operations may include the clinician selecting Drug A with a base concentration of 250 mg/mL from the "Drug" selection list (e.g., using input/output components 152). In this use case, the processes of the flow of operations may include pump 102 and/or server 160 recognizing Drug A with a concentration of 250 mg/mL as a drug requiring GR intermittent base concentration setup screens. In this use case, the processes of the flow of operations may include the clinician entering a dose of 100 mg (e.g., using input/output components 152). In this use case, the processes of the flow of operations may include pump 102 or server 160 calculating a dose volume of 0.4 mL and pre-populating a duration field with a default value of 30 min. In this use case, the processes of the flow of operations may include pump 102 or server 160 may auto-calculate a rate of 0.8 mL/h and prepopulate a volume to be infused (VTBI) field with 0.4 mL. In this use case, the processes of the flow of operations may include the clinician selecting a microinfusion prime option (e.g., using input/output components 152) and accepting the default values of 0.2 mL prime at 5 mL/h. (2.4 min). In this use case, the processes of the flow of operations may include the clinician selecting (e.g., using input/output components 152) the post flush option and default flush volume of 0.2 mL. In this use case, the processes of the flow of operations may include pump 102 or server 160 recalculating the flow rate to 1.2 mL/h with a dose volume of 0.4 mL and duration of 20 minutes. A flush rate may also be 1.2 mL/h with a volume of 0.2 mL and a duration of 10 min, for a total delivery time of 30 min. In this use case, at this stage system 100 is completely programmed and awaiting injection of Drug A.

In this use case, the processes of the flow of operations may include pump 102 beginning to monitor downstream pressure and prompting the user to inject Drug A into the injection port of valve 118. In this use case, the processes of the flow of operations may include the clinician removing the medication syringe with Drug A, 100 mg/0.4 mL, from the pharmacy packaging. In this use case, in some implementations, the clinician manually moves the flow control valve shroud to expose the injection port. In this use case, the processes of the flow of operations may include the clinician attaching the Drug A syringe to the injection port. In this use case, the processes of the flow of operations may include the clinician manually beginning to prime 0.4 mL Drug A solution in a retrograde fashion into retrograde set 104. In this use case, the processes of the flow of operations may include pump 102 sensing an increase in pressure at the downstream pressure sensor due to the manual priming and begins to run (pump) backwards to accommodate the retrograde flow of saline from the lower line. The flush solution is displaced into the flush fluid container 106 (e.g., a syringe or a bag). Pump 102 or server 160, in the background, tracks total retrograde volume and stops when the maximum retrograde volume is reached or when the pressure returns to a baseline pressure. In this use case, the volume determined from the set ID is 2 mL.

In this use case, the processes of the flow of operations may include the clinician continuing to inject the entire 0.4 mL of Drug solution A into the line until the medication syringe is empty. In this use case, the processes of the flow of operations may include pump 102 activating a START key (e.g., a physical or virtual button associated with display 150 or components 152). In this use case, the processes of the flow of operations may include the clinician detaching the medication syringe (and, in some implementations, manually moving the flow control shroud to cover the injection port). In this use case, the processes of the flow of operations may include the clinician verifying (e.g., using input/output components 152) the infusion parameters and pressing the START key. In this use case, the processes of the flow of operations may include pump 102 delivering 0.2 mL of prime from the syringe set. Display 150 may be operated to indicate the delivery of "Drug A 100 mg—Prime at 5 mL/h."

In this use case, the processes of the flow of operations may include pump 102 automatically switching rates to deliver 0.4 mL of Drug A from the medication syringe. Display 150 may indicate the delivery of "Drug A 100 mg" at 1.2 mL/h per normal intermittent workflow. In this use case, the processes of the flow of operations may pump 102 automatically switching to 0.2 mL of flush solution at 1.2 mL/h. Display 150 may indicate delivery of Drug A 100 mg—FLUSH. In this use case, the processes of the flow of operations may include pump 102 providing an infusion complete audio/visual alarm. The alarm condition is logged and reported by pump 102 or server 160. In this use case, the processes of the flow of operations may include the clinician observing, or pump 102 determining, that the dose is completely delivered and flushed, then stopping infusion. In this use case, the processes of the flow of operations may include pump 102 putting the Drug A channel into the idle state and allowing the option of repeating Drug A as previously programmed if the infusion went to the complete state. In this use case, the processes of the flow of operations may include pump 102 or server 160 logging and reporting delivery of Drug A 100 mg, Rate=1.2 mL/h, VTBI=0.4 mL and VI=0.4 mL, prime volume of 0.2 mL delivered at 5 mL/h and dose started at time of switchover from Prime. Pump 102 and/or server 160 may also log and report any additional flush programmed at the end of the infusion.

Figure 12:
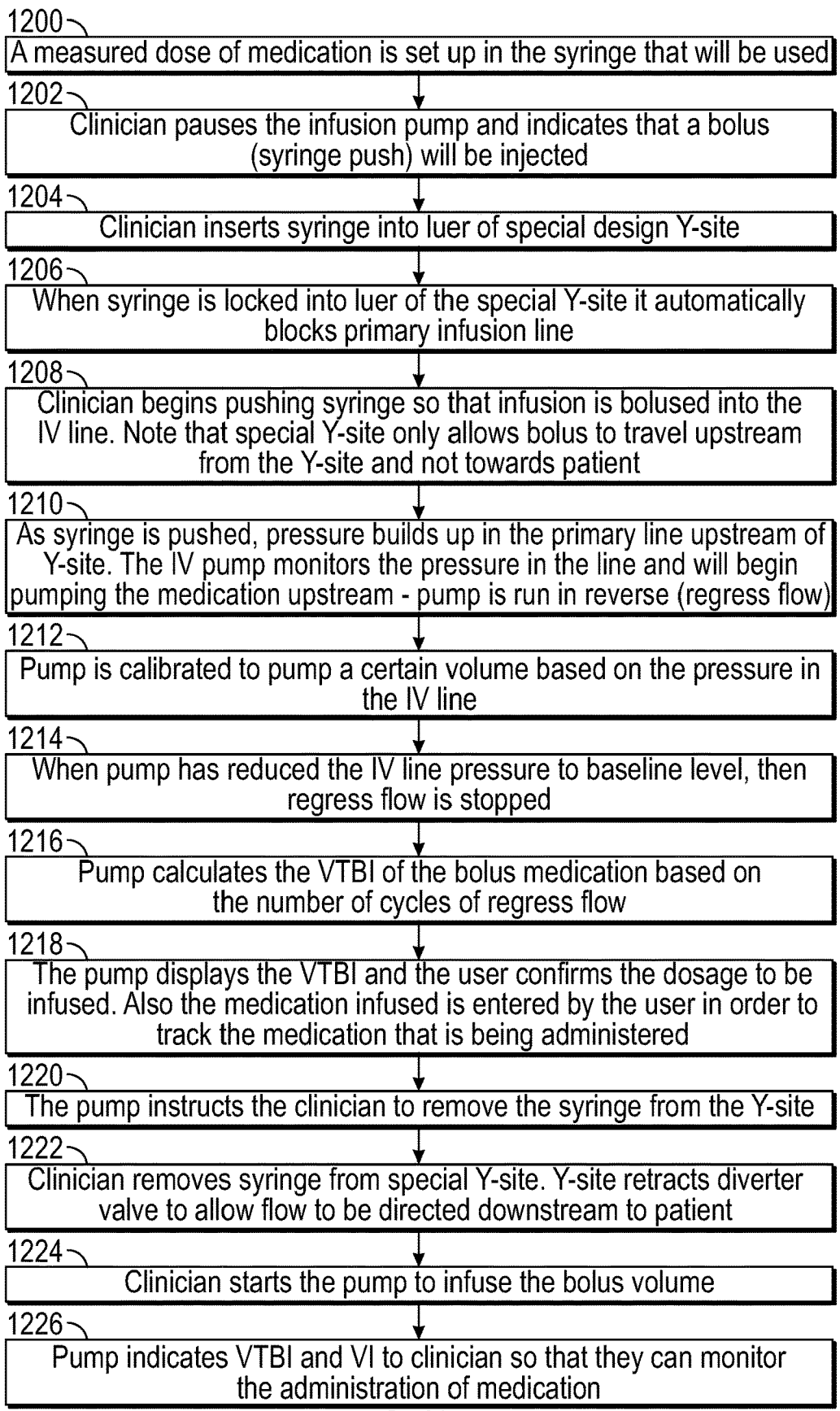
FIG. 12 is a flow chart showing illustrative operations for providing a medical fluid to a patient using a system for administering medical fluid to a patient using an IV pump and an IV set having a flow control valve and a flush container according to certain aspects of the present disclosure.
Figure 13:
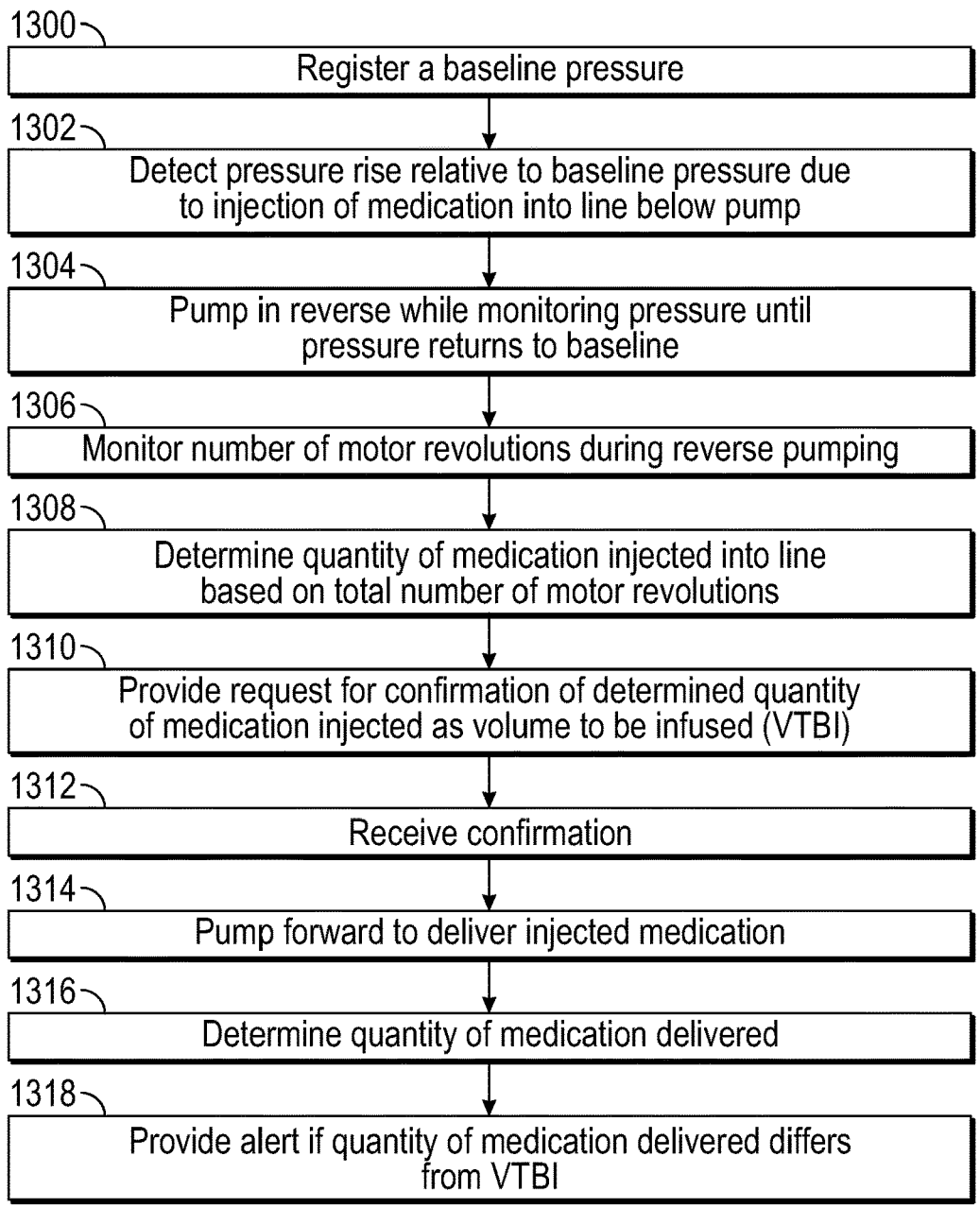
FIG. 13 is a flow chart showing illustrative operations of an infusion pump during operations for providing a medical fluid to a patient using a system for administering medical fluid to a patient using an IV pump and an IV set having a flow control valve and a flush container according to certain aspects of the present disclosure.
Figure 14:
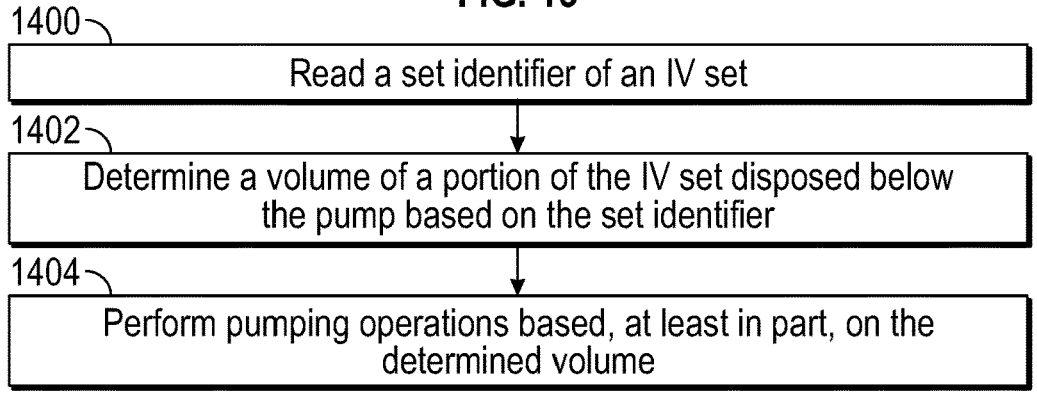
FIG. 14 is a flow chart showing illustrative operations of an infusion pump during operations for providing a medical fluid to a patient using a system for administering medical fluid to a patient using an IV pump and an IV set having a set identifier according to certain aspects of the present disclosure.

Turning now to the remaining drawings, FIGS. 2-11 show various aspects of a system for microinfusion of medical fluids according to various embodiments. The systems shown and described in connection with FIGS. 1-11, and additionally the flow charts of FIGS. 12-14 may be used, for example, to perform the operations of the exemplary use case described above, or other use cases, and may provide various advantages as described above and in connection with the figures below. FIGS. 1, 2, 8, 9, and 11 show configurations of system 100 at various stages before, during, and after a microinfusion to patient 121. Accordingly, each of FIGS. 1, 2, 8, 9, and 11 include a graphical indicator 122 indicating the amount of the desired fluid that has been provided to the patient at the illustrated stage of that figure.

FIG. 1 shows an initial configuration of system 100 with set 104 connected to patient 121 and interface portion 112 coupled to pump 102.

Figure 2:
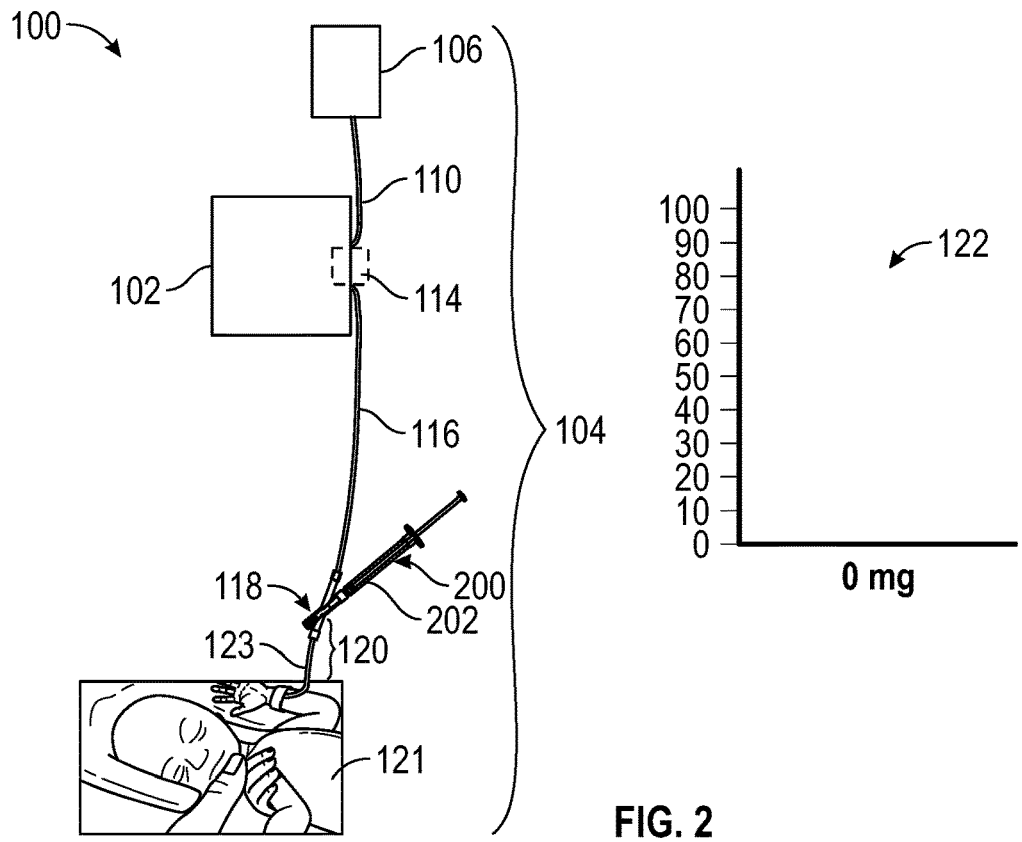
FIG. 2 illustrates the system of FIG. 1 with a syringe attached to the flow control valve according to certain aspects of the present disclosure.

FIG. 2 shows a configuration of system 100 with a syringe 200 containing a medical fluid 202 attached at an input port of flow control valve 118. In the configuration of FIG. 2, the first fluid pathway between tubing segment 116 and tubing 123 is blocked and a fluid pathway from syringe 200 into tubing 116 through flow control valve 118 is generated. Flow control valve 118 may have a manual mechanical switch that blocks the first fluid pathway while exposing the input port for access or may include internal switching components such as a sliding valve as described hereinafter that block the first fluid pathway responsive to the attachment of the syringe to the input port.

Figure 3:
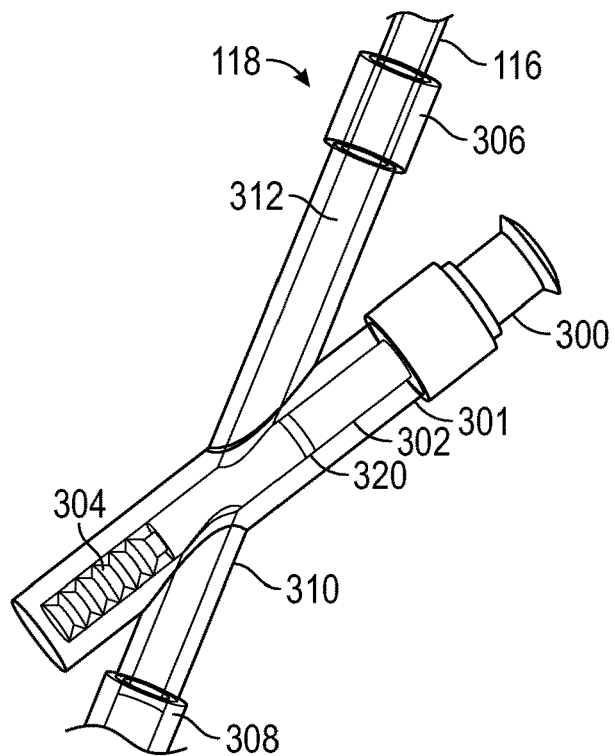
FIG. 3 illustrates a side view of a flow control valve according to certain aspects of the present disclosure.
Figure 4:
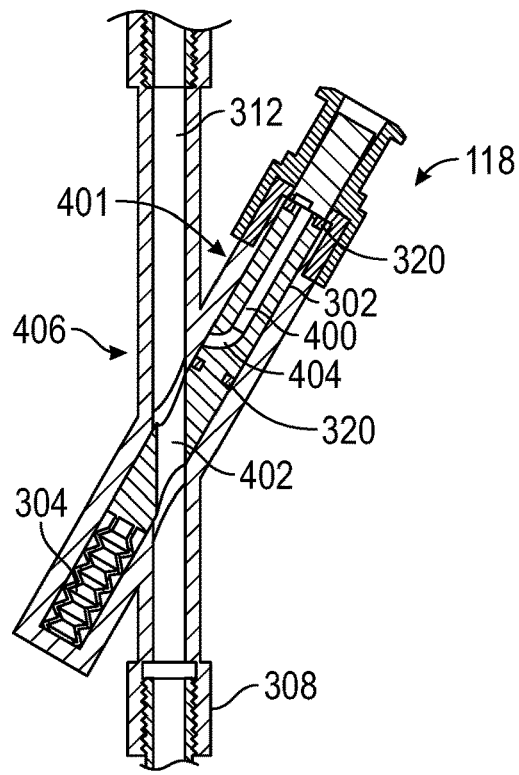
FIG. 4 illustrates a cross-sectional side view of a flow control valve according to certain aspects of the present disclosure.

FIGS. 3-5 show various views of an exemplary implementation of flow control valve 118 in which the flow control valve includes internal switching components that block the first fluid pathway responsive to the attachment of the syringe to the input port.

As shown in FIG. 3, flow control valve 118 may include a syringe port such as Luer fitment 300 for a y-port 301 integrally formed with a main housing 310 that forms the first fluid pathway 312 from tubing 116 (coupled at pump-side or input interface 306) to the patient interface components (coupled at patient-side or output interface 308). FIG. 3 is a side view of flow control valve 118 with a transparent housing that allows viewing of an internal sliding valve member 302 and a spring 304. As shown in FIGS. 3 and 4, sliding valve member 302 may include one or more seals 320 that help control the flow of fluid through flow control valve 118.

FIG. 4 is a cross-sectional side view of flow control valve 118 in which it can be seen that first fluid pathway 312 may extend through an opening 402 in sliding valve member 302 when member 302 is in a first position (e.g., when spring 304 is extended and no syringe is attached to fitment 300). Sliding valve member 302 may include another opening 400 that, when a syringe is coupled to fitment 300 such that the syringe presses sliding valve member 302 from y-port portion 401 downward to compress spring 304, a curved portion 404 of opening 400 couples the syringe to an upper portion 406 of main housing 310 and thus to tubing 116. Opening 402 may have an axis that is parallel to the axis of main housing 310 and non-parallel and non-perpendicular to the longitudinal axis of valve member 302 and y-port 301. Opening 400 may include an elongated portion that extends along or parallel to the longitudinal axis of y-port 301 and valve member 302 and curved portion 404, fluidly coupled to the elongated portion, that curves away from the longitudinal axis of y-port 301 and valve member 302 to couple the elongated portion to the upper portion of main housing 310 when spring 304 is compressed responsive to coupling of a syringe to fitment 300. In a configuration in which sliding member 302 is pressed from y-port 301 through main housing 310 such that opening 400 couples the syringe to the upper portion 406, seals 320 may be positioned to block flow from upper portion 406 to patient-side interface 308.

FIG. 5 shows an interfacing portion 500 of syringe 200 being coupled to fitment 300 of flow control valve 118. The direction 504 to the patient is also indicated.

FIG. 6 shows another view of flow control valve 118 in a position in which opening 402 is positioned within main housing 310 to allow fluid flow along first fluid pathway 312. As shown in FIGS. 4 and 6, sliding valve member 302 may substantially fill the volume within the central bore of y-port portion 401 such that a very low residual volume of medical fluid is trapped in the valve. In this way, substantially all of the medical fluids intended for the patient are delivered to the patient. In various other embodiments, different configurations for valve 118 may be used. However, a primary characteristic of all of the embodiments is a very low residual volume of medical fluid trapped in the valve. FIG. 7 is a cross-sectional side view of sliding valve member 302 showing openings 400 and 402 and showing a second fluid flow pathway 700 through the curved portion of opening 400 through valve member 302.

Figure 8:
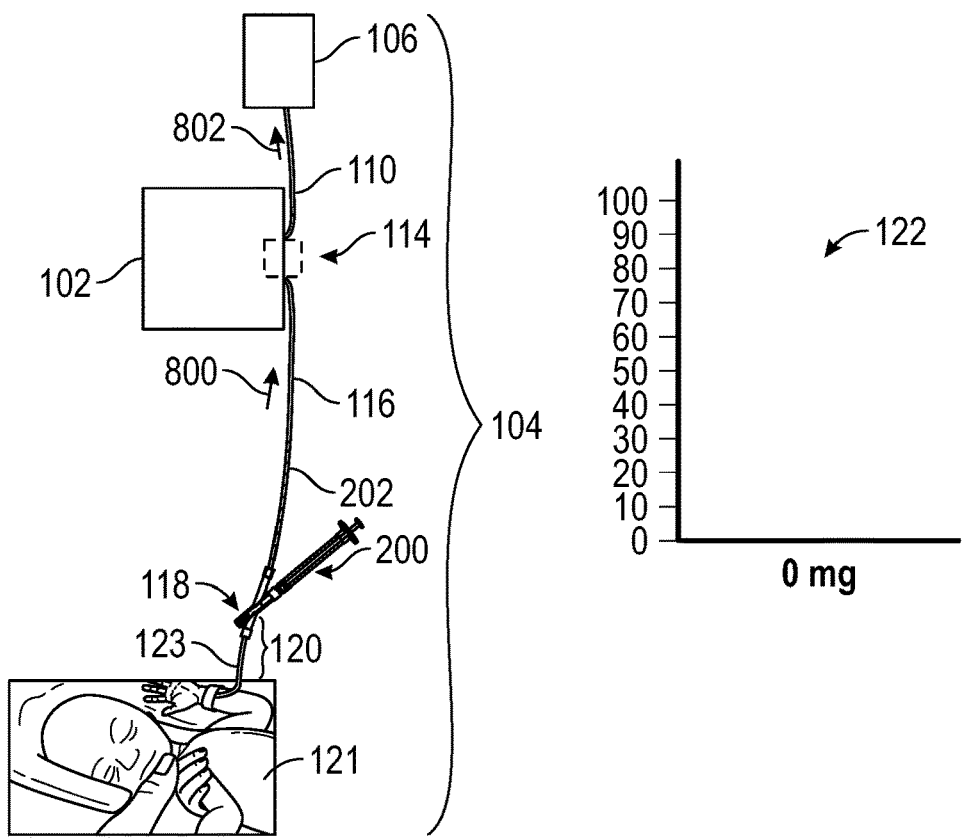
FIG. 8 illustrates the system of FIG. 2 in a configuration in which a medical fluid from the syringe flows from the flow control valve into a tubing section disposed between the flow control valve and the infusion pump using a reverse operation of the pump, according to certain aspects of the present disclosure.
Figure 9:
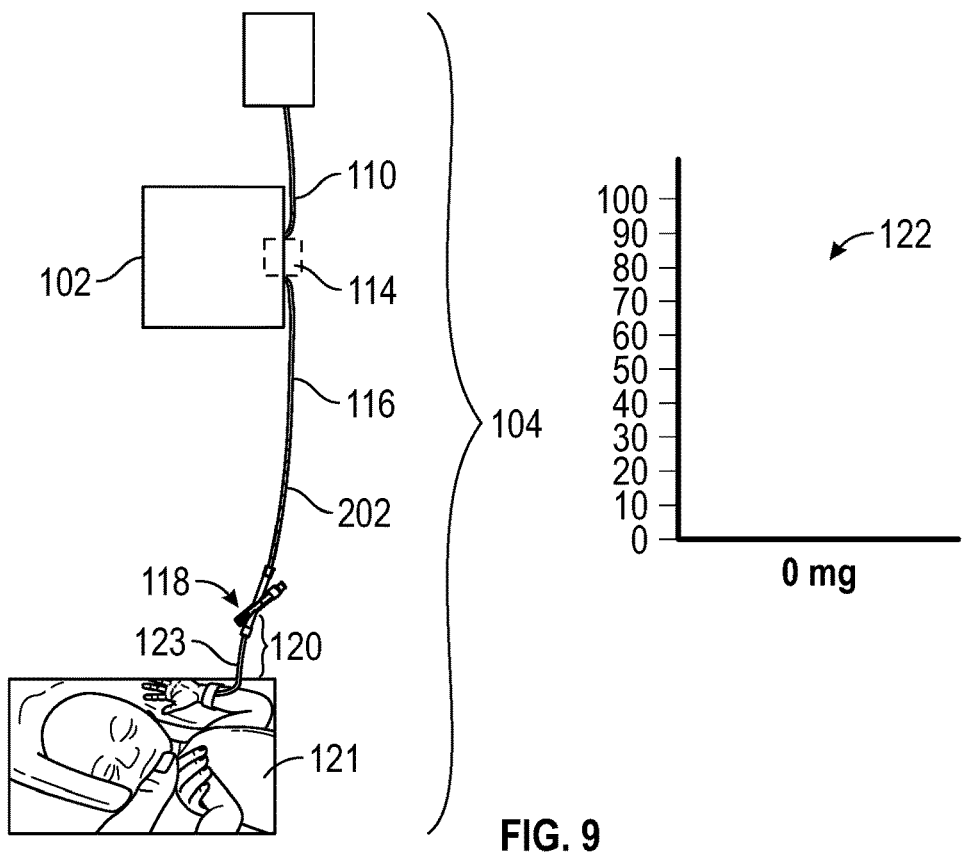
FIG. 9 illustrates the system of FIG. 8 following removal of the syringe from the flow control valve according to certain aspects of the present disclosure.
Figure 10:
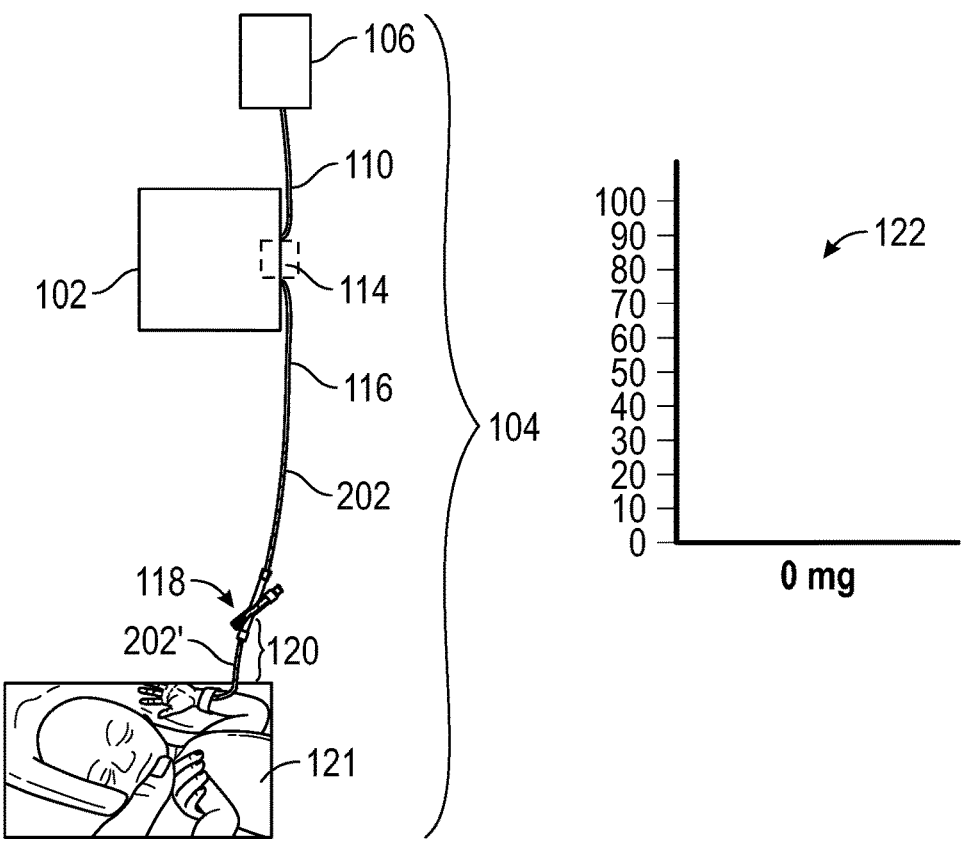
FIG. 10 illustrates the system of FIG. 9 in a configuration in which the infusion pump has pumped the medical fluid through the flow control valve into a tubing section disposed between the flow control valve and the patient according to certain aspects of the present disclosure.

FIG. 8 shows system 100 in a configuration in which medical fluid 202 has been injected from syringe 200, through flow control valve 118, into tubing 116 (in direction 800) with the assistance of pump 102 pumping in reverse (e.g., in response to a detection of increased back pressure) to move fluid (e.g., saline) within tubing 110 and/or 116 into flush container 106 (in direction 802). FIG. 9 shows system 100 in a configuration in which syringe 200 has been removed from flow control valve 118 (to open the first fluid pathway) and medical fluid 202 remains in tubing 116. FIG. 10 shows system 100 in a configuration in which a priming phase of the medical fluid delivery has been completed (e.g., to pump any fluid in portion 120 to the patient, at a same, or higher rate than the infusion rate for the medical fluid) so that a portion 202' of the medical fluid 202 is disposed in portion 120 and ready for delivery to the patient.

Figure 11:
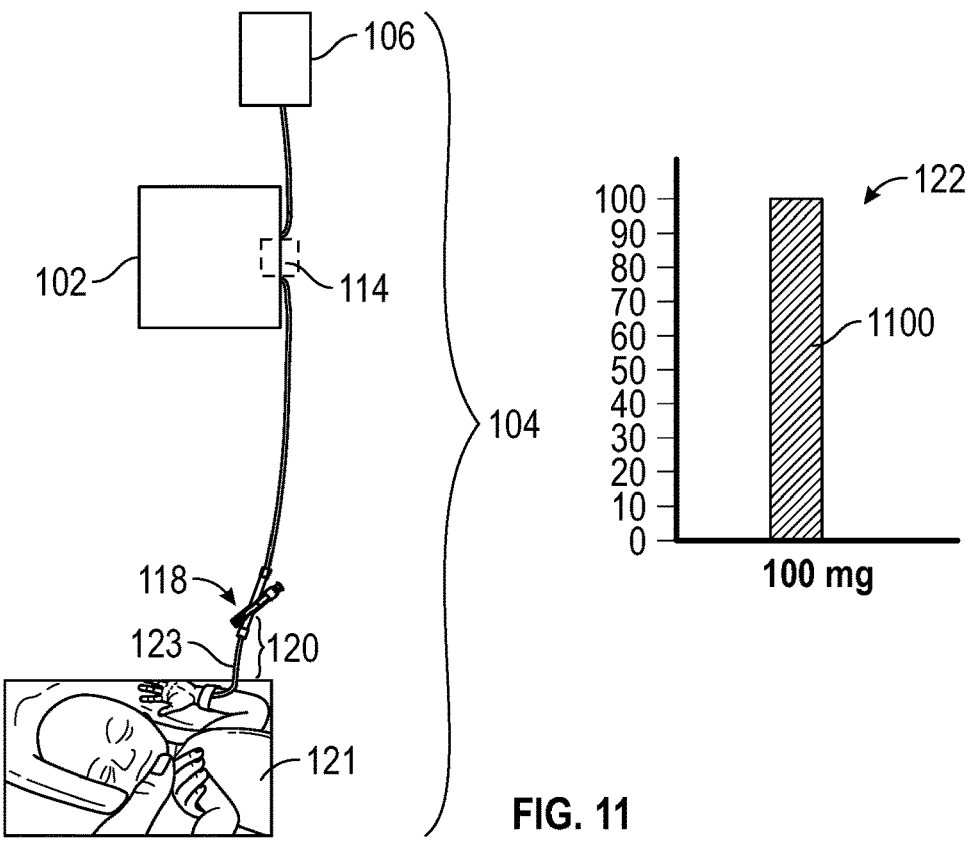
FIG. 11 illustrates the system of FIG. 10 following delivery of the medical fluid to the patient according to certain aspects of the present disclosure.

FIG. 11 shows system 100 in a configuration in which the medical fluid 200 has been pumped, using pump 102, through flow control valve 118 to the patent. A graphical indicator 122 (which may be displayed for a clinician during on a display of pump 102 during any or all phases of the infusion) indicates the amount 1100 of the medical fluid that has been delivered to the patient. Because pump 102 knows the volume of IV set 104 (particularly the volume below the pump), pump 102 can monitor, at all times, the amount of medical fluid that has been infused to the patient. This monitored data can be stored at the pump and/or provided to a remote system of storage and/or analysis. The actual volume infused can also be cross-checked against the expected (programmed) volume. In some embodiments, set 104 (e.g., valve 118) may include a clip or dummy port to which the expended syringe can be attached to facilitate tracking of the infused medication.

Illustrative operations that may be performed for microinfusion of a medical fluid to a patient using, for example, system 100 described above, are shown in FIG. 12.

At block 1200, a measured dose of medication is set up in the syringe that will be used (see, e.g., syringe 200).

At block 1202, a clinician pauses the infusion pump (e.g., using input/output components 152) and indicates that a bolus (syringe push) will be injected.

At block 1204, the clinician inserts a syringe into a Luer such as fitment 300 of a Y-site flow control valve (see, e.g., valve 118 of FIGS. 2-7).

At block 1206, when the syringe 200 is locked into the Luer 300 of the valve 118, the flow control valve (e.g., valve member 302) automatically blocks the primary infusion line (e.g., by moving opening 402 away from first pathway 312 as in the configuration of FIG. 7).

At block 1208, the clinician begins pushing the syringe 200 so that infusion is bolused into the IV line (e.g., into portion 116). Because of the arrangement of openings 400 and 402 and seals 320, valve 118 only allows bolus to travel upstream from valve 118 and not towards the patient 121.

At block 1210, as the syringe is pushed, pressure builds up in the primary line upstream of valve 118. Pump 102 monitors the pressure in the line and begins pumping the medication upstream from syringe 200 through valve 118 (e.g., the pump is run in reverse (regress flow)).

At block 1212, the pump is calibrated to pump a certain volume based on the pressure in the IV line (e.g., until the pressure returns to a baseline pressure) or based on a known volume of IV set 104 and/or a known amount of fluid in syringe 200 (e.g., based on a set identifier for IV set 104 and/or a medication identifier on syringe 200).

At block 1214, when pump 102 has reduced the IV line pressure to baseline level, then regress flow is stopped automatically by pump 102 (e.g., when pump 102 detects the pressure being reduced to the baseline pressure).

At block 1216, pump 102 calculates the volume to be infused (VTBI) of the bolus medication based on the number of cycles of regress flow (e.g., the number of cycles of a pump motor). Although the operations associated with blocks 1212, 1214, and 1216 are described as using the IV line pressure and number of cycles of regress flow to determine the VTBI, in some embodiments (e.g., embodiments in which a set identifier is provided to the pump), based on stored information at the pump such as the dose and the concentration of the drug, the pump may automatically look up or otherwise determine the volume of the set below the pump and can perform pumping operations (e.g., regress flow pumping) based, at least in part, on the known volume. The volume of the set may be stored at the pump (e.g., in memory 156) or in a remote database (e.g., database 162) along with volumes (and other IV set information) for various IV set types, each associated with a corresponding one of a plurality of set identifiers.

At block 1218, pump 102 may use display 150 to display the VTBI and may use input/output components 152 to receive user confirmation of the dosage to be infused. The medication to be infused may be entered by the user (e.g., using input/output components 152) in order to track the medication that is being administered. In various embodiments, pump 102 reconciles the amount of fluid injected below the pump via valve 118 with the expected volume of the dose (e.g., based on a known concentration of a drug in the injected fluid) and alerts the user (e.g., by providing an audio alert, a visual alert, and/or preventing further operations of the pump) if there is a significant discrepancy between the expected dose volume and the actual amount of injected fluid.

At block 1220, the pump provides instructions (e.g., on display 150) to the clinician to remove the syringe from valve 118.

At block 1222, the clinician removes the syringe from valve 118. Responsive to removal of syringe 200, a diverter valve (e.g., sliding valve member 302) may retract due to extension of spring 304 to allow flow to be directed downstream to the patient via path 312 through opening 402.

At block 1224, the clinician starts pump 102 (e.g., using input/output components 152) to infuse the bolus volume.

At block 1226, pump 102 indicates (e.g., using display 150) the VTBI and volume infused (VI) to the clinician so that they can monitor the administration of medication.

Illustrative operations that may be performed, particularly by an infusion pump such as pump 102, for microinfusion of a medical fluid to a patient using, for example, system 100 described above are shown in FIG. 13.

At block 1300, pump 102 may register a baseline pressure in IV set 104 (e.g., by sensing the pressure in interface portion 112 of tubing 108 with a sensor such as a pressure sensor included in components 158).

At block 1302, pump 102 may detect (e.g., using the sensor) a pressure rise relative to the baseline pressure. The pressure rise may be due to the injection of medication into line 116 below pump 102 via valve 118.

At block 1304, pump 102 may begin, responsive to the detection of the rise in pressure, to operate pump components 158 in reverse while monitoring the pressure in the line, until the pressure returns to the baseline pressure.

At block 1306, the number of motor revolutions (or other pump attributes) may be monitored (e.g., counted) by pump 102 (e.g., processing circuitry 154).

At block 1308, pump 102 (e.g., processing circuitry 154) may determine the quantity of medication injected into the line via valve 118 based on the total number of motor revolutions.

At block 1310, pump 102 may provide (e.g., using display 150) a request for confirmation of the determined quantity of medication injected as the volume to be infused (VTBI).

At block 1312, pump 102 may receive clinician confirmation of the VTBI via input/output components 152.

At block 1314, pump 102 may return to normal flow downstream by operating pumping components 158 to pump forward to deliver the medication.

At block 1316, pump 102 may determine (e.g., based on the total number of forward motor revolutions) the quantity of medication delivered to the patient.

At block 1318, pump 102 may provide an alert (e.g., using display 150 or other visual or audio components) if the quantity of medication delivered differs from the VTBI.

As discussed herein in connection with various implementations and embodiments, pump 102 may operate to retrograde pump a medication from a syringe via valve 118, and deliver the medication, based on set volume information determined from a set identifier. Illustrative operations that may be performed, for microinfusion of a medical fluid to a patient using, for example, system 100 described above are shown in FIG. 14.

At block 1400, an infusion pump, such as pump 102 of system 100, that is coupled to an IV set (e.g., IV set 104 having a flush container 106, tubing 108 extending from the flush container 106 to a patient interface 120, a pump interface portion 112/114 of the tubing disposed between the flush container 106 and the patient interface 120 and configured to be coupled to and manipulated by the pump, a flow control valve 118 coupled to the tubing at a location between the pump interface portion 112/114 and the patient interface 120, and a set identifier 159) may read the set identifier. Reading the set identifier may include optically scanning a bar code or other visual code, receiving a alpha-numerical entry of the set identifier input by a clinician, wirelessly reading a radio frequency identification (RFID) tag associated with the IV set 104 or otherwise receiving the set identifier with processing circuitry 154.

At block 1402, pump 102 may determine a volume of a portion of the IV set disposed below the pump. For example, pump 102 may include a memory such as memory 156 that stores IV set information for a plurality of IV set types, each associated with a corresponding one of a plurality of set identifiers. Pump 102 may determine the volume by selecting one of the plurality of IV set types corresponding to the read set identifier of the IV set and by extracting the volume from the IV set information of the selected one of the plurality of IV set types. As another example, a server such as server 160 that is remote from and in communication with pump 102, may include a database such as database 162 that stores IV set information for a plurality of IV set types, each associated with a corresponding one of a plurality of set identifiers. Pump 102 may determine the volume by providing the read set identifier to the server 160 and receiving the volume from server 160. Server 160 may receive the read set identifier from the pump 102, select one of the plurality of IV set types corresponding to the received set identifier and extract the volume from the IV set information of the selected one of the plurality of IV set types.

At block 1404, pump 102 may perform pumping operations based, at least in part, on the determined volume. Performing pumping operations based, at least in part, on the determined volume may include comparing an expected dose volume with an actual amount of a medical fluid that has been injected into the IV set via the flow control valve. Performing pumping operations based, at least in part, on the determined volume may include determining the expected dose volume based on a known concentration of a drug in the injected medical fluid as determined based on the set identifier. Pump 102 may perform pumping operations based, at least in part, on the determined volume by comparing an expected dose volume with an actual amount of a medical fluid that has been injected into the IV set via the flow control valve and providing an alert if there is a medically significant discrepancy between the expected dose volume and the actual amount.

The subject technology is illustrated, for example, according to various aspects described above. The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A disposable intravenous (IV) set, comprising:
   a main housing having an upper portion and a lower portion, the upper portion configured to connect to a fluid tubing providing a fluid from a fluid container, the lower portion configured to connect to a patient interface device;
   a y-port housing formed with an exterior of the main housing and comprising a lower end and an upper end extending, from the lower end and from a location between the upper portion and the lower portion of the main housing, to a syringe port located in the upper end of the y-port housing; and
   an elongated sliding valve within and traversing the y-port housing and configured to slide from a first position, at which a first opening through the sliding valve is positioned within the y-port housing at an intersection of the y-port housing and the main housing to form a first fluid pathway between the upper portion and the lower portion of the main housing through the first opening, to a second position, at which the first fluid pathway is blocked and a second opening through the sliding valve is positioned within the y-port housing to form a second fluid pathway between the upper portion of the main housing and the syringe port.

2. The disposable IV set of claim 1, wherein the second fluid pathway comprises a first portion that extends from the syringe port toward the main housing along a longitudinal axis of the y-port housing, and a second portion fluidly coupled to the first portion and that curves away from the first portion and away from the longitudinal axis of the y-port housing to fluidly couple to the upper portion of the main housing and form the second fluid pathway when the sliding valve is in the second position.

3. The disposable IV set of claim 2, further comprising:
a spring disposed within the lower end of the y-port housing opposite the syringe port and the upper end of the y-port housing,
wherein the spring is configured to engage the sliding valve to cause the sliding valve to be positioned in the first position when a syringe is not engaged with the syringe port, and to compress when the sliding valve is moved toward the lower end responsive to a coupling of a syringe with the syringe port,
wherein the coupling of the syringe with the syringe port causes the sliding valve to be compressed against the spring to move the sliding valve to the second position whereby the second fluid pathway is formed, and a decoupling of the syringe from the syringe port causes the sliding valve to retract due to extension of the spring to move to the first position whereby the first fluid pathway is formed.

4. The disposable IV set of claim 2, wherein the sliding valve moves along the longitudinal axis of the y-port housing, and the longitudinal axis of the y-port housing is offset at an angle with respect to the main housing.

5. The disposable IV set of claim 4, further comprising:
one or more seals positioned between an outer surface of the sliding valve and an interior surface of the y-port housing, and configured to block fluid flow from the upper portion of the main housing to the lower portion of the main housing when the sliding valve is in the second position.

6. The disposable IV set of claim 5, wherein the one or more seals are arranged around the sliding valve so that, based on the angle, when the sliding valve is in the second position, the one or more seals prevents fluid flow between the lower portion of the main housing and the upper portion of the main housing, and prevents fluid flow between the lower portion of the main housing and the upper end of the y-port housing.

7. The disposable IV set of claim 2, wherein the patient interface device comprises a venous access device.

8. A flow control valve, comprising:
a diverter housing positioned between an upper portion of a fluid line and a lower portion of the fluid line, the diverter housing comprising a lower end and an upper end extending away from the lower end and offset at an angle from an exterior of the fluid line to a port located in the upper end of the diverter housing; and
a diverter having an elongated profile within the diverter housing and configured to move within and traverse the diverter housing from a first position, at which a first opening through the diverter is positioned at an intersection of the diverter and the fluid line to form a first fluid pathway between the upper portion and the lower portion of the fluid line, to a second position, at which the first fluid pathway is blocked and a second fluid pathway is formed between the upper portion of the fluid line and the port in the upper end of the diverter housing.

9. The flow control valve of claim 8, wherein the second fluid pathway comprises a first portion that extends from the port toward the fluid line along a longitudinal axis of the diverter housing, and a second portion fluidly coupled to the first portion and that curves away from the first portion and away from the longitudinal axis of the diverter housing to fluidly couple to the upper portion of the fluid line and form the second fluid pathway when the diverter is in the second position.

10. The flow control valve of claim 9, further comprising:
a spring disposed within the lower end of the diverter housing opposite the port and the upper end of the diverter housing,
wherein the lower end of the diverter housing extends away from the fluid line and the spring is configured to engage the diverter to cause the diverter to be positioned in the first position when a fluid interface is not engaged with the port, and to compress when the diverter is moved toward the lower end responsive to a coupling of a fluid interface with the port,
wherein the coupling of the fluid interface with the port causes the diverter to be compressed against the spring to move the diverter to the second position whereby the second fluid pathway is formed, and a decoupling of the fluid interface from the port causes the diverter to retract due to extension of the spring to move to the first position whereby the first fluid pathway is formed.

11. The flow control valve of claim 9, wherein the diverter moves along the longitudinal axis of the diverter housing, and the longitudinal axis of the diverter housing is offset at an angle with respect to the fluid line.

12. The flow control valve of claim 11, further comprising:
a seal positioned between an outer surface of the diverter and an interior surface of the diverter housing, and configured to block fluid flow from the upper portion of the fluid line to the lower portion of the fluid line when the diverter is in the second position.

13. The flow control valve of claim 12, wherein the seal is arranged around the diverter so that, based on the angle, when the diverter is in the second position, the seal prevents fluid flow between the lower portion of the fluid line and the upper portion of the fluid line, and prevents fluid flow between the lower portion of the fluid line and the upper end of the diverter housing.

14. The flow control valve of claim 8, wherein the port comprises a luer fitting or a syringe fitting.

15. The flow control valve of claim 8, further comprising:
a main housing integrally formed with the diverter housing and having a first protrusion connected to the upper portion of the fluid line, and a second protrusion connected to the lower portion of the fluid line, the main housing and the first and second protrusions being parallel with the fluid line, and a longitudinal axis of the diverter housing being offset at an angle from the main housing and first and second protrusions.

16. A method, comprising:
providing a flow control valve housing configured to be positioned between an upper portion of a fluid line and a lower portion of a fluid line, the flow control valve housing comprising a first elongated housing and a second elongated housing offset from an exterior of the first elongated housing by an angle, the first elongated housing having an upper port for connecting to the upper portion of the fluid line, and a lower port for connecting to the lower portion of the fluid line, the second elongated housing comprising a lower end and an upper end extending away from the lower end and the fluid line to a syringe port located in the upper end;

providing an elongated sliding valve within and traversing the second elongated housing and configured to slide from a first position, at which a first opening through the sliding valve is positioned at an intersection of the first elongated housing and the second elongated housing to form a first fluid pathway between the upper portion and the lower portion of the fluid line through the first opening, to a second position, at which the first fluid pathway is blocked and a second opening through the sliding valve is positioned to form a second fluid pathway between the upper portion of the fluid line and the syringe port.

17. The method of claim 16, wherein the second fluid pathway comprises a first portion that extends from the syringe port toward the first elongated housing along a longitudinal axis of the second elongated housing, and a second portion fluidly coupled to the first portion and that curves away from the first portion and away from the longitudinal axis of the second elongated housing to fluidly couple to the upper portion of the first elongated housing and form the second fluid pathway when the sliding valve is in the second position.

18. The method of claim 17, wherein the lower end of the second elongated housing comprises a spring, wherein the spring is configured to engage the sliding valve to cause the sliding valve to be positioned in the first position when a syringe is not engaged with the syringe port, and to compress when the sliding valve is moved toward the lower end responsive to a coupling of a syringe with the syringe port.

19. The method of claim 18, further comprising:
coupling a syringe with the syringe port, and causing the sliding valve to compress the spring and move to the second position whereby the second fluid pathway is formed; and decoupling of the syringe from the syringe port, and causing the sliding valve to retract from the second position and move to the first position due to extension of the spring whereby the first fluid pathway is formed.

20. The method of claim 18, further comprising:
coupling the flow control valve housing to a fluid line; and
coupling the fluid line to an IV set.

* * * * *